United States Patent [19]

Schneider et al.

[11] Patent Number: 4,981,862

[45] Date of Patent: Jan. 1, 1991

[54] TETRAHYDROBENZOTHIAZOLES, AND THE PREPARATION AND USE THEREOF

[75] Inventors: Claus Schneider; Herbert Merz; Rainer Sobotta, all of Ingelheim am Rhein; Rudolf Bauer, Wiesbaden; Joachim Mierau, Mainz; Günter Schingnitz, Bad Kreuznach, all of Fed. Rep. of Germany

[73] Assignee: Boehringer Ingelheim KG, Ingelheim am Rheine, Fed. Rep. of Germany

[21] Appl. No.: 287,829

[22] Filed: Dec. 20, 1988

Related U.S. Application Data

[63] Continuation of Ser. No. 57,582, Jun. 2, 1987, abandoned.

[30] Foreign Application Priority Data

Jun. 21, 1986 [DE] Fed. Rep. of Germany ....... 3620813

[51] Int. Cl.$^5$ .................. C07D 277/68; A61K 31/425
[52] U.S. Cl. ...................................... 514/367; 548/163
[58] Field of Search ......................... 548/163; 514/367

[56] References Cited

U.S. PATENT DOCUMENTS 4,731,374 3/1988 Griss .................... 514/367

Primary Examiner—Robert Gerstl
Attorney, Agent, or Firm—D. E. Frankhouser; Mary-Ellen M. Timbers; Alan Stempel

[57] ABSTRACT

Tetrahydrobenzothiazole derivatives of the formula

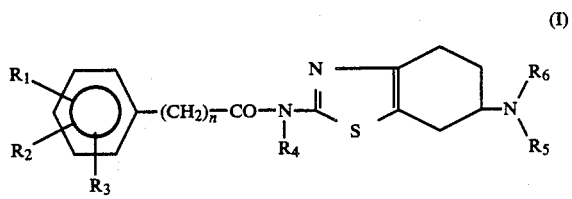

wherein n is 1, 2 or 3 and $R_1$, $R_2$, $R_3$, $R_4$, $R_5$ and $R_6$ are defined substituents, said derivatives (I) being suitable as active compounds for treating parkinsonism or Parkinson's Disease.

6 Claims, No Drawings

TETRAHYDROBENZOTHIAZOLES, AND THE PREPARATION AND USE THEREOF

This is a continuation of application Serial No. 057,582, filed Jun. 2, 1987

The invention relates to new tetrahydrobenzothiazole derivatives, the preparation thereof, and the use thereof as medicaments in pharmaceutical preparations.

The novel tetrahydrobenzothiazole derivatives of this invention are represented by the formula:

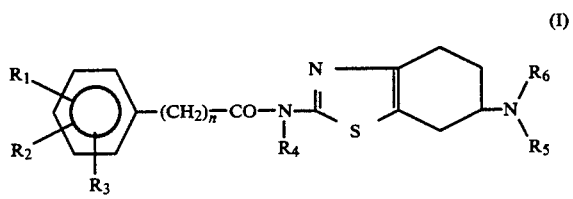

(I)

in which
n is 1, 2 or 3;
$R_1$ is H, F, Cl, Br, $CH_3$, $C_2H_5$, $OCH_3$, $OC_2H_5$, OH or $CF_3$;
$R_2$ is H, Cl, $CH_3$, $OCH_3$, $OC_2H_5$ or OH;
$R_3$ is H or $NH_2$;
$R_4$ is H, $CH_3$ or $C_2H_5$; and
$R_5$ and $R_6$ are each H, $C_{1-4}$ alkyl, phenyl-substituted $C_{1-3}$-alkyl, allyl or propargyl;
and the nontoxic pharmaceutically acceptable acid-addition salts thereof.

$R_1$ preferably represents H, $OCH_3$, OH, Cl, Br, $CH_3$ or $C_2H_5$; $R_2$ preferably represents H, $OCH_3$ or Cl; $R_4$ preferably represents H or $CH_3$; $R_5$ preferably represents H, $C_{1-3}$-alkyl, allyl or phenethyl; and $R_6$ preferably represents H, $C_{1-3}$-alkyl or allyl. Those compounds in which $R_1$ denotes $OCH_3$ or OH, $R_2$, $R_3$ and $R_4$ denote H, and $R_5$ and $R_6$ denote H or $C_{1-3}$-alkyl are to be particularly emphasised.

The index n preferably represents 2 or 3, and, most preferably, 2.

If at least one of the radicals $R_1$ to $R_4$ has a meaning other than hydrogen, then the $R_4$-position of the phenyl function is preferably substituted, whereas a further substituent which may be present is preferably in the 3-position.

Typical radicals of the formula

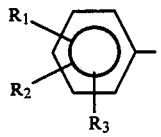

(II)

are, for example, 4-methoxyphenyl, 4-chlorophenyl, 4-hydroxyphenyl, 3,4-dimethoxyphenyl, 4-hydroxy-3-methoxyphenyl, 4-methylphenyl and 3,5-dichloro-4-aminophenyl.

The new compounds can exist as racemates or pure enantiomers, but also as mixtures of the enantiomers in any ratios. In general, one of the enantriomers of the racemate is more active than the other.

The new compounds can be prepared by methods which are known per se:
1. Reductive amination of a compound of the formula

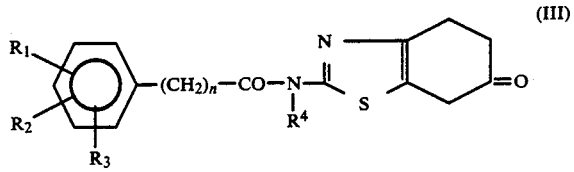

(III)

in which n and $R_1$ to $R_4$ have the above-mentioned meaning, using a compound of the formula

(IV)

in which $R_5$ and $R_6$ have the above meaning, and a reducing agent.

Reducing agents which can be used are hydrogen and hydrogenation catalysts, for example Raney nickel, platinum, palladium, or complex hydrides, for example sodium borohydride. Suitable reaction media are polar organic solvents which are inert under the reaction conditions, for example lower aliphatic alcohols, such as methanol or ethanol. The reaction preferably takes place with gentle cooling (for example when $NaBH_4$ is used as the reducing agent), and, if appropriate, with warming and under pressure when using hydrogen/catalyst.

2. For the preparation of compounds of the formula I which contain a phenolic OH group, an appropriate ether, for example the methylether, can also be subjected to conventional ether cleavage, for example using a boron bromide. Suitable solvents are, for example, halogenated hydrocarbons, such as methylene chloride or ethylene chloride. The reaction is expediently carried out at room temperature.

3. For the preparation of compounds of the formula I in which neither radical $R_5$ or $R_6$ denotes hydrogen, an appropriate compound in which $R_6$ is hydrogen can be reacted with the compound of the formula

X—$R'_6$ (V)

in which $R'_6$ has the same meaning as $R_6$ apart from hydrogen, and X represents a group which can be eliminated on introduction of $R'_6$ into the amino group, for example a halogen atom.

If the starting materials are not known, they can be prepared by conventional methods.

Compounds of the formula III, for example, can be prepared by reacting acyl chlorides of the formula

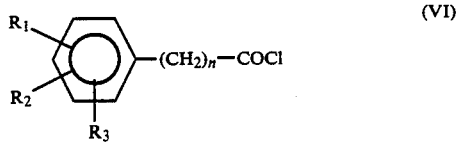

(VI)

in which n, $R_1$, $R_2$ and $R_3$ have the above meaning, with 6-oxo-2-aminotetrahydrobenzothiazole with heating, preferably in the presence of a tertiary aliphatic amine, such as triethylamine, in an inert organic solvent.

The final products of the formula I, which are initially obtained as bases, can be converted into nontoxic pharmaceutically acceptable acid-addition salts by conventional treatment with appropriate inorganic or organic acids, and, correspondingly, acid-addition salts which are obtained initially can be converted into bases or salts of other acids.

Typical acid-additional salts of physiologically readily tolerated acids are for example, the hydrochloride, hydrobromide, sulphate, methanesulphonate, succinate, fumarate, maleate, citrate and formate among others.

The compounds according to the invention contain a chiral center and are therefore generally produced as racemates, which can then be conventionally separated, if desired, into the enantiomers using conventional optically active acids, for example using tartaric acid, O,O-dibenzoyl tartaric acid, camphorsulphonic and α-methoxyphenylacetic acid.

If an optically active starting material is employed, for example in process 2 or 3, the enantiomers can also be obtained directly.

The new compounds are suitable as medicaments, in particular for the treatment of Parkinson's disease or Parkinsonism. They can furthermore be used for prolactin inhibition and for treating schizophrenia.

The compounds according to the invention exhibit a particularly favourable profile of action. It is to be emphasised that
  the action lasts for a long time (up to about 20 hours),
  emesis does not occur in the therapeutic dose range, and
  low adrenergic action is observed.

Compounds having such a profile of action have not been described hitherto.

The action can be demonstrated on apes (MPTP model).

Determination of the Anti-Parkinsonism and Anti-Parkinson Action

The discovery of the neurotoxin 1-methyl-4-phenyl-1,2,3,6-tetrahydro-pyridine (MPTP) (Langston et al., Science 219, 979 (1983)) has made available an animal model for Parkinson's disease.

In its clinical, pathological, biochemical and pharmacological character, the irreversible, neurological clinical picture initiated in humans and in apes by MPTP substantially resembles idiopathic Parkinson's disease (Markey et al., Nature 311, 464 (1984)). The cause of this agreement is that MPTP selectively destroys that small group of dopaminergic nerve cells in the cerebral substantia nigra that is also destroyed by degenerative processes in naturally occurring Parkinson's disease. It is also debated whether the cause of idiopathic Parkinson's disease is also MPTP, or a similar chemical compound, produced in the organism (Snyder, S. H., Nature 311, 514 (1984)). Possibly caused by the specific metabolism of MPTP, the clinical character of the MPTP-Parkinson picture has the term only been detectable in apes, in addition to in humans.

The MPTP model realised in rhesus apes is therefore suitable, to an excellent extent, for testing the action of anti-Parkinson medicaments. MPTP (1×0.15 mg/kg i.m. daily for 3 days, 3 days pause, 1×0.30–0.40 mg/kg daily for 3 days) was administered to rhesus apes; they exhibited the following symptoms: the animals were akinetic and not able to take water and feed. They exhibited a typical stoop; cataleptic states occurred from time to time. The extremities exhibited a rigour, which was interrupted by chronic cramps during passive movement. It was generally not possible to initiate voluntary movements of the rump and the extremities by the strongest, painful stimulae.

A few minutes after the intramuscular administration of the compound according to the invention, the first voluntary movements occur, which are followed by gradual, substantial normalisation of motoriscity. The animals are then able to take food. They support themselves properly in the cages, which also applies with respect to vigilence and species-specific behaviour. Occasional temporary, slight passive tremor and reduction of physical strength are recorded as residual symptoms.

In some cases, the action of the compounds only falls off after about 20 hours, and the animals again take on the Parkinson symptoms described above; readministration of the compound again leads to improvement or substantial relief of the clinical pathological symptom. The advantageous action of the compounds can thus be reproduced.

For therapeutic administration of the new compounds, conventional galenic preparations in unit dosage form are prepared, for example, tablets, coated tablets, suppositories, powders, suspensions and solutions. The daily dose is 0.1 to 10 mg/kg, preferably 0.5 to 5 mg/kg of body weight; it is administered in one or several individual doses.

Accordingly, the subject invention provides a pharmaceutical composition for treating parkinsonism or Parkinson's Disease comprising a therapeutically effective amount of a compound of formula I and a pharmaceutically acceptable carrier. It also provides a method of treating parkinsonism or Parkinson's Disease which comprises administering to an individual afflicted with same a therapeutically effective amount of a compound of formula I, preferably in a unit dosage form of said pharmaceutical composition.

Examples of medicament preparations according to the invention (data in parts by weight):

Coated Tablets 5.0 parts of active compound according to the invention
33.5 parts of lactose
10.0 parts of maize starch
1.0 part of gelatin
0.5 part of magnesium stearate The powdered components active compound, lactose and maize starch are granulated with aqueous gelatin solution and dried. The granules are mixed with the magnesium stearate and compressed to form coated tablet cores weighing 50 mg and are coated by known methods.

Suppositories 10 parts of active compound according to the invention
1690 parts of suppository material (for example Witepsol W 45)

The finely powdered substance is distributed uniformly, by means of a homogeniser, in the molten suppository material, cooled to 40° C. Suppositories weighing 1.7 g are shaped from the mixture.

The Examples below are intended to illustrate the invention in greater detail:

EXAMPLE 1

2-(4-Methoxyphenylpropionyl)amino-6-n-propylamino-4,5,-6,7-tetrahydrobenzothiazole (a) Preparation of the racemate 15.1 g (0.09 mol) of 6-oxo-2-amino-tetrahydrobenzothiazole and 20.5 g (0.1-mol) of 4-methoxyphenylpropionyl chloride are refluxed for 2 hours in 450 ml of tetrahydrofuran and 0.1 mol of triethylamine, subsequently poured onto ice and extracted with ethyl acetate. After drying, 2-(4-methoxyphenylpropionyl)amino-6-oxo-tetrahydrobenzothiazole (17.5 g) crystallises out on concentrating, and, is dissolved in methanol and is reductively aminated, without further purification, in an autoclave using propylamine (Raney nickel, 5 bar, 60° C.). After filtering off the catalyst under suction, the solvent is removed by distillation. The residue crystallises from i-propyl ether. Yield: 12.5 g (63% of theory)

Base: Melting point 105°–106° C. (recrystallised from ethyl acetate)

Dihydrochloride: Melting point 259°–261° C.

(b) Resolution of the racemate 3.75 g (0.025 mol) of L-(+)-tartaric acid [Aldrich: $[\alpha_n^{20}]$ 12° (c=20 H$_2$O)] are added to a suspension of the product obtained according to (a) (9.3 g, 0.025 mol) in 200 ml of water. The mixture is refluxed for 15 minutes and filtered. The colourless crystals which precipitate after one day are filtered off under suction. This L-(+)-tartaric acid salt is recrystallised five times from 75 ml of water. The optical rotation $[\alpha]_D^{20}$ of $-45.5°$ C. (c=1, CH$_3$OH) of the liberated base does not change further on further recrystallisation.

From the pure L-(+)-tartaric acid salt, the base is liberated using concentrated ammonia and extracted with ethyl acetate. After washing and drying (magnesium sulphate), the solvent is removed in vacuo. The dihydrochloride' of the (−)-enantiomer crystallises through treatment with ethereal hydrochloric acid.

Yield: 0.9 g, melting point 261°–262° C.
$[\alpha]_D^{20}$ $-41.1°$ (c=1, CH$_3$OH)

EXAMPLE 2

2-(4-Hydroxyphenylpropionyl)amino-6-n-propylamino-4,5,6,7-tetrahydrobenzothiazole 9.6 g (0.026 mol) of the compound obtained according to Example 1 are dissolved in 300 ml of methylene chloride and stirred for 3 hours at 15° C. with 90 ml of boron tribromide. Water is added to the reaction mixture, which is then rendered alkaline using concentrated ammonia. The organic phase is extracted with methylene chloride dried and concentrated. The dihydrobromide of the title compound is obtained from the residue using ethanolic hydrobromic acid.

Yield: 4.95 g (49% of theory)
melting point 228°–229° C.

Further Examples:

| No. | R$_1$ | R$_2$ | R$_3$ | R$_4$ | R$_5$ | R$_6$ | n | Mp. (°C.) |
|---|---|---|---|---|---|---|---|---|
| 3 | 4-OCH$_3$ | H | H | H | C$_2$H$_5$ | H | 2 | 224–225 (Fumarate) |
| 4 | 4-OCH$_3$ | H | H | H | CH$_3$ | H | 2 | 202–204 (Fumarate) |
| 5 | 4-OH | H | H | H | C$_2$H$_5$ | H | 2 | 164–165 (Dihydrobromide) |
| 6 | 4-OH | H | H | H | CH$_3$ | H | 2 | 239–240 (Base) |
| 7 | 4-CH$_3$ | H | H | H | n-C$_3$H$_7$ | H | 2 | >260 (Fumarate) |
| 8 | 2-OCH$_3$ | H | H | H | n-C$_3$H$_7$ | H | 2 | 216–217 (Oxalate) |
| 9 | 3-OCH$_3$ | H | H | H | n-C$_3$H$_7$ | H | 2 | |
| 10 | 4-OCH$_3$ | H | H | CH$_3$ | n-C$_3$H$_7$ | H | 2 | |
| 11 | 4-OCH$_3$ | H | H | H | n-C$_3$H$_7$ | C$_6$H$_5$<br>\|<br>C$_2$H$_5$ | 2 | |
| 12 | 4-OCH$_3$ | H | H | H | n-C$_3$H$_7$ | n-C$_3$H$_7$ | 2 | |
| 13 | 4-Cl | H | H | H | n-C$_3$H$_7$ | H | 2 | |
| 14 | 3-Cl | 4-Cl | H | H | n-C$_3$H$_7$ | H | 2 | |
| 15 | H | H | H | H | n-C$_3$H$_7$ | H | 2 | >260 (Fumarate) |
| 16 | 4-OH | H | H | H | CH$_3$ | CH$_3$ | 2 | 259–260 Dihydrobromide) |
| 17 | 4-CF$_3$ | H | H | H | n-C$_3$H$_7$ | H | 2 | >260 |
| 18 | 4-OCH$_3$ | H | H | H | CH$_3$ | CH$_3$ | 2 | >260 (Monohydrochloride) |
| 19 | 4-OCH$_3$ | H | H | H | H | H | 2 | 115–117 (Base) |
| 20 | 4-OCH$_3$ | 3-OCH$_3$ | H | H | n-C$_3$H$_7$ | H | 2 | |
| 21 | 4-C$_2$H$_5$ | H | H | C$_2$H$_5$ | CH$_2$=CH<br>\|<br>CH$_2$ | CH$_2$=CH<br>\|<br>CH$_2$ | 2 | |
| 22 | 3-Cl | 5-Cl | 4-NH$_2$ | H | n-C$_3$H$_7$ | H | 2 | |
| 23 | 4-CF$_3$ | H | H | H | CH$_3$ | C$_2$H$_5$ | 2 | |
| 24 | 2-F | H | 4-OCH$_3$ | H | i-C$_3$H$_7$ | H | 2 | |
| 25 | 4-OH | 2-CH$_3$ | H | H | n-C$_4$H$_9$ | H | 1 | |
| 26 | 4-OCH$_3$ | H | H | H | n-C$_3$H$_7$ | H | 3 | 93–94 Dihydrochloride |

-continued

| No. | R₁ | R₂ | R₃ | R₄ | R₅ | R₆ | n | Mp. (°C.) |
|---|---|---|---|---|---|---|---|---|
| 27 | 4-Br | H | H | CH₃ | t-C₄H₉ | H | 2 | |
| 28 | 3-OH | H | H | H | i-C₃H₇ | H | 3 | |
| 29 | 4-OCH₃ | H | H | H | n-C₃H₇ | n-C₃H₇ | 3 | |
| 30 | 4-OC₂H₅ | H | H | H | n-C₄H₉ | H | 2 | |
| 31 | 4-C₂H₅ | H | H | H | n-C₄H₉ | H | 2 | |
| 32 | 4-C₂H₅ | H | H | H | i-C₄H₉ | H | 3 | |
| 33 | 3-OC₂H₅ | 4-OC₂H₅ | H | H | n-C₄H₉ | H | 3 | |
| 34 | 3-OH | 5-OH | H | H | C₂H₅ | CH₃ | 2 | |
| 35 | 4-OCH₃ | H | H | H | n-C₄H₉ | n-C₄H₉ | 2 | |
| 36 | n-OCH₃ | H | H | H | n-C₃H₇ | H | 1 | 167-168 Difumarate |
| 37 | 3-OCH₃ | 4-OCH₃ | H | H | C₂H₅ | C₂H₅ | 3 | |

We claim:
1. Tetrahydrobenzothiazole of the formula:

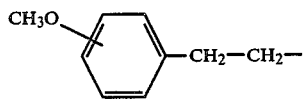

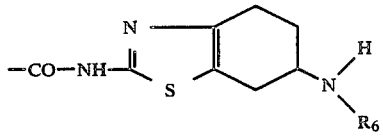

wherein R₆ is C₁-C₄ alkyl, its individual enantioners or the racemate, or a pharmaceutically acceptable acid addition salt thereof.

2. The tetrahydrobenozthiazole as recited in claim 1.

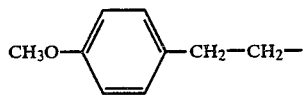

-continued

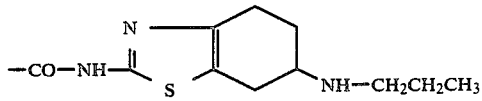

its individual enantiomers or the racemate, or a pharmaceutically acceptable acid addition salt thereof.

3. A pharmaceutical composition of matter comprising a therapeutically effective amount of a compound as recited in claim 1 for treatment of parkinsonism or Parkinson's Disease and a pharmaceutically acceptable carrier.

4. A pharmaceutical composition of matter comprising a therapeutically effective amount of a compound as recited, in claim 2 for treatment of parkinsonism or Parkinson's Disease and a pharmaceutically acceptable carrier.

5. A method of treating parkinsonism or Parkinson,'s Disease which comprises administering to an individual afflicted with same a therapeutically effective amount of a compound as recited in claim 1.

6. A method of treating parkinsonism or Parkinson's Disease which comprises administering to an individual afflicted which same a therapeutically effective amount of a compound as recited in claim 2.

* * * * *